(12) United States Patent
Soltes et al.

(10) Patent No.: US 7,563,824 B2
(45) Date of Patent: Jul. 21, 2009

(54) CLATHRATE COMPLEXES FORMED BY HYALURONIC ACID DERIVATIVES AND USE THEREOF AS PHARMACEUTICALS

(75) Inventors: Ladislav Soltes, Bratislava (SK); Bohumil Steiner, Malacky (SK); Eva Machova, Bratislava (SK); Grigorij Kogan, Bratislava (SK); Slavomir Bystricky, Bratislava (SK); Raniero Mendichi, Tribiano (IT); Viktor Bauer, Samorin (SK); Mojmir Mach, Sastin Straze (SK); Juraj Alfordi, Bratislava (SK); Eva Stratilova, Bratislava (SK)

(73) Assignee: Italian Joint Stock Company, Abano Terme (Province of Padova) (IT)

( * ) Notice: Subject to any disclaimer, the term of this patent is extended or adjusted under 35 U.S.C. 154(b) by 595 days.

(21) Appl. No.: 10/220,934

(22) PCT Filed: Mar. 12, 2001

(86) PCT No.: PCT/EP01/02722

§ 371 (c)(1),
(2), (4) Date: Apr. 1, 2003

(87) PCT Pub. No.: WO01/66601

PCT Pub. Date: Sep. 13, 2001

(65) Prior Publication Data

US 2004/0076680 A1   Apr. 22, 2004

(30) Foreign Application Priority Data

Mar. 10, 2000   (SK) .................................. 358-2000

(51) Int. Cl.
*A61K 47/00* (2006.01)
(52) U.S. Cl. ................. 514/772.1; 514/772; 514/772.3; 514/777; 424/422; 424/423; 424/426

(58) Field of Classification Search ............. 424/488; 514/58

See application file for complete search history.

(56) References Cited

U.S. PATENT DOCUMENTS

| | | | | |
|---|---|---|---|---|
| 4,636,524 A | * | 1/1987 | Balazs et al. | 514/781 |
| 4,834,985 A | * | 5/1989 | Elger et al. | 424/488 |
| 5,134,127 A | * | 7/1992 | Stella et al. | 514/58 |
| 5,382,571 A | * | 1/1995 | Granger et al. | 514/58 |
| 5,470,512 A | * | 11/1995 | Noji et al. | 264/4.1 |
| 5,690,961 A | * | 11/1997 | Nguyen | 424/488 |
| 6,309,669 B1 | * | 10/2001 | Setterstrom et al. | 424/486 |

OTHER PUBLICATIONS

Soltes et al., "Cyclodextin derivative of hyaluronan" Carbohydrate Polymers, 39 (1999) 17-24.*
C&EN Jul. 24, 2006 "Chemistry Grads Post Gains in 2005".*
Soltes et al "Molecular characterization of two host-guest associating hyaluronan derivatives" Biomedical chromatography 2003 376-384.*

(Continued)

*Primary Examiner*—Eric E. Silverman
(74) *Attorney, Agent, or Firm*—Abelman, Frayne & Schwab

(57) ABSTRACT

A clathrate formed by: a hyaluronic acid derivative (a), a hyaluronic acid derivative (b1) different from (a), and being able to form a clathrate with (a) and/or a component (b2) not containing a hyaluronic acid moiety but being able to form with (a) a clathrate and its use in the pharmaceutical field.

22 Claims, 3 Drawing Sheets

OTHER PUBLICATIONS

Soltes et al. "Associating hyaluronan derivatives: a novel horizin in viscosupplamentation of osteoarthritic joints" Chemistry and Biodiversity 2004 468-472.*

Lee S. Simon, "Viscosupplementation Therapy with Intra-Articular Hyaluronic Acid" *Rheumatic Disease Clinics of North America* Osteoarthritis, vol. 25, No. 2, pp. 345-357 (May 1999).

Jaques G. Peyron, "Intraarticular Hyaluronan Injections in the Treatment of Osteoarthritis: State-of-the-Art Review", *The Journal of Rheumatology*, vol. 20, Supplement 39, pp. 10-15 (1993).

Kikuchi et al., "Effect of High Molecular Weight Hyaluronan on Cartilage Degeneration in a Rabbit Model of Osteoarthritis", *Osteoarthritis and Cartilage*, vol. 4, pp. 99-110, (1996).

Balazs, "Hyaluronic Acid in Synovial Fluid. I. Molecular Parameters of Hyaluronic Acid in Normal and Arthritic Human Fluids", *Arthritis & Rheumatism*, vol. 10, No. 4, pp. 357-376, (Aug. 1967).

Larsen et al., "Drug Delivery Systems Using Hyaluronan and Its Derivatives", *Advanced Drug Delivery Reviews*, 7 pp. 279-293 (1991).

Nishimura et al., "Role of Chondroitin Sulfate—Hyaluronan Interactions in the Viscoelastic Properties of Extracellular Matrices & Fluids", *Biochimica et Biophysica Acta*, 1380, pp. 1-9 (1998).

Nimrod et al., "Absorption, Distribution, Metabolism, and Excretion of Bacteria—Derived Hyaluronic Acid in Rats & Rabbits", *Journal of Ocular Pharmacology*, vol. 8, No. 2, pp. 161-172 (1992).

Brown et al., "Turnover of Hyaluronan in Synovial Joints: Elimination of Labelled Hyaluronan from the Knee Joint of the Rabbit", *Experimental Physiology*, No. 76, pp. 125-134 (1991).

Drobnik, "Hyaluronan in Drug Delivery", *Advanced Drug Delivery Reviews*, vol. 7, pp. 295-308 (1991).

Al-Assaf, "The Enhanced Stability of the Cross-Linked Hylan Structure to Hydroxyl (OH) Radicals Compared with the Uncross-Linked Hyaluronan", *Radiat. Phys. Chem.*, vol. 46, No. 2, pp. 207-217 (1995).

Wobig et al., "Viscosupplementation with Hylan G-F 20: A 26-Week Controlled Trial of Efficacy & Safety in the Osteoarthritic Knee", *Clinical Therapeutics*, vol. 20, No. 3, pp. 410-423 (1998).

* cited by examiner

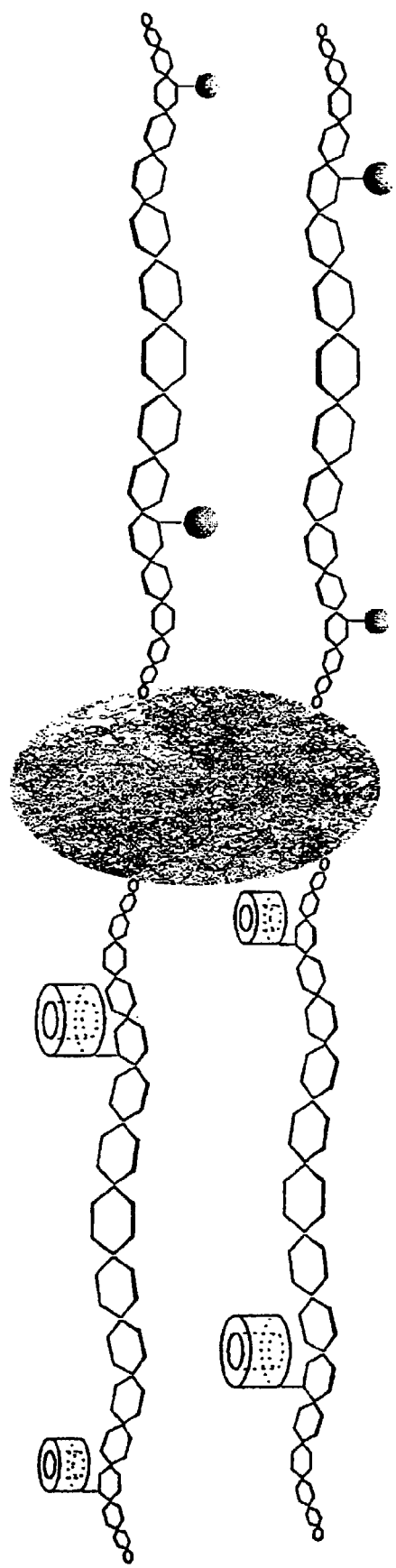

CLATHRATE COMPLEXES FORMED BY HYALURONIC ACID DERIVATIVES AND USE THEREOF AS PHARMACEUTICALS

FIELD OF THE INVENTION

The invention deals with clathrate complexes between hyaluronic acid derivatives obtained by means of physico-chemical crosslinking of the derivatives of high-molecular-weight hyaluronic acid or salts thereof.

TECHNOLOGICAL BACKGROUND

Arthritis is currently one of the most frequent diseases of the human population. Among approximately one hundred different types of arthritis, osteoarthritis (OA) belongs to those which management requires the most financial investments and thus imposes a major burden for the economy [L. S. Simon, *Osteoarthritis* 25 (1999) 345].

In OA the synovial fluid becomes more abundant and less viscous while the concentration of synovial hyaluronan (HA) as well as its molecular weight decrease. [J. G. Peyron, J. Rheum. 20, *Suppl*. 39 (1993) 10]. These changes are kept co-accountable for the subsequent accelerated degradation of the cartilage. Intra-articular (injection) administration of the high-molecular-weight HA to the patients (this therapy is currently called "viscosupplementation") is described as an effective procedure in the treatment of traumatized arthritic joints [T. Kikuchi et al., *Osteoarthritis and Cartilage* 4 (1996) 99].

The average molecular weight of synovial HA of healthy humans lies in the range $(1.6-10.9)\times10^6$ Da; while its concentration equals 2-3 mg/ml [E. A. Balazs et al., *Arthritis Rheum*. 10 (1967) 357]. Molecular weight values of commercially available HA preparations obtained from various (natural) sources such as e.g. bacteria *Streptococcus zooepidemicus* or *Streptococcus equii*, rooster combs, etc., vary in the range from hundreds of thousands to ca. 1-2 million Da (FIG. 1). High-molecular-weight HA binds up to 1000 times more water than is its own mass and forms pseudoplastic, elasto-viscous solutions, that behave as soft gels that reveal so-called shear-dependent viscosity and frequency-dependent elasticity [N. E. Larsen and E. A. Balazs, *Adv. Drug Delivery Rev*. 7 (1991) 279]. At the low magnitude of the shear tension, solutions of high-molecular-weight HA reveal high viscosity and low elasticity; while at the increasing values of shear tension the solutions become more elastic [L. S. Simon, *Osteoarthritis* 25 (1999) 345]. Such non-Newtonian behavior of synovial fluid is essential for the lubrication of joints during the (fast) movement. The cartilage surface is covered by a thin film of SF that smoothens (fine) unevenness of the articular structure. Deficiency of this layer leads to increased friction coefficient between the moving parts of the joint which results in strong pain [M. Nishimura et al., *Biochim. Biophys. Acta* 1380 (1998) 1]. Ultrapure (ready for injection application) preparations of the elastoviscous solutions of the hyaluronan sodium salt (HEALON®; Pharmacia, Uppsala, Sweden), obtained from the rooster combs, have found extended application especially in ophthalmology (viscosurgery) [A. Nimrod et al, *J. Ocular Pharmacol*. 8 (1992) 161], as well as in rheumatology (viscosupplementation) [J. G. Peyron, *J. Rheumatology* 20, *Suppl*. 39, (1993) 10; T. Kikuchi et al, *Osteoarthritis and Cartilage* 4 (1996) 99].

Recently another preparation for the intra-articular administration to OA patients was approved in the USA and some other countries. This new product containing high-molecular-weight HA originating from the rooster combs, named HYLAN® (Biomatrix Inc., Ridgefield, N.J., USA) included additionally cross-linked HA [L. S. Simon, *Osteoarthritis* 25 (1999) 345]. The rationale (of this innovation) is the fact that the period of time during which the intra-articularly deposited hyaluronan exerts its activity is relatively short. The biological half-life of HA after its intra-articular application into the rabbit's knee joint was ~13 hours [T. J. Brown et al, *Exp. Physiol*. 76 (1991) 125]. (The turnover of endogenous hyaluronan in the joints lasts 12-48 hours [J. Drobnik, *Adv. Drug Delivery Rev*. 7 (1991) 295].) The water-soluble HYLAN®s with ultra-high molecular weight (on average around $6\times10^6$ Da) that were prepared by chemical cross-linking of HA with formaldehyde reveal a significantly longer biological half-life period [L. S. Simon, *Osteoarthritis* 25 (1999) 345]. HYLAN®s prepared in this way, i.e. using a chemical cross-linking represent the most effective viscosupplementation (bio)materials. In the other (water-insoluble) HYLAN® preparations (gels, membranes, microparticles) HA is cross-linked through the introduced vinylsulfone groups with resulting formation of the "infinite" poly(macro)molecular network [N. E. Larsen and E. A. Balazs, *Adv. Drug Delivery Rev*. 7 (1991) 279].

However summarizing all literature data on the pre-clinical and clinical trials that involved injections of HYLAN® solutions [N. E. Larsen and E. A. Balazs, *Adv. Drug Delivery Rev*. 7 (1991) 279; S. Al-Assaf et al, *Radiat. Phys. Chem*. 46 (1995) 207; M. Wobig et al., *Clin. Ther*. 20 (1998) 410; L. S. Simon, *Osteoarthritis* 25 (1999) 345] one can come to a conclusion that along with their remarkable useful properties such as biocompatibility, (bio)degradability, (complete) resorption, non-immunogenicity, very low and rare pyrogenicity, their obvious drawback is a very high viscosity. Due to the fact that intra-articularly (through injection) administered ultra-high-molecular-weight hyaluronans (HYLAN®s) are enormously viscous pseudoplastic gels, their penetrability into the narrow clefts/slits of the damaged articular structure is (obviously) largely impaired.

TECHNICAL PROBLEM

The need was felt to possess (have available) hyaluronic acid having high molecular weight, with the aforementioned advantages and at the same time not having an excessive viscosity.

SUMMARY OF THE INVENTION

The Applicants have unexpectedly found that it is possible to overcome the aforementioned drawbacks by applying a novel procedure of physico-chemical cross-linking of the appropriate derivatives of the high-molecular-weight hyaluronic acid or its salts.

As a matter of fact, the present invention relates to a clathrate formed by:
  a hyaluronic acid derivative (a),
  a hyaluronic acid derivative (b1) different from (a), and being able to form a clathrate with (a) and/or
  a component (b2) not containing a hyaluronic acid moiety but being able to form with (a) a clathrate;

The required increase of the molecular weight of HA, or formation of the (three-dimensional) polymeric network due to the formation of clathrate complexes will preferably take place in situ in the locus/site of the desired action. In this way the suitable fluid preparation for viscosupplementation (e.g. for OA treatment) can be obtained, or a soft/resilient and even a solid/rigid gel (suitable e.g. for "remodeling" of the missing (portion of a) tissue. The process for preparing the aforementioned clathrate complexes deals with the so-called (self)-associating supramolecular compounds. The more efficient viscosupplementation therapy will be achieved using an original approach that includes either:
i) two subsequent intra-articular injections of the associating components (a), (b1) and/or (b2). As a result of increased penetrability and permeability of the low-viscous injected fluids, upon their association, a desired viscosupplementation product is formed directly in the target location), or
ii) the intra-articular administration of the aforementioned associating components along with a suitable low-molecular-weight substance, namely an active ingredient, primary role of which is to block (compete with) the process of association. (Upon the injection of such a "cocktail", molecules of the (low-molecular-weight) agent (drug) initially completely blocks the process of association, however upon elimination (excretion) of the drug from the articular environment the desired (in situ) self-association of the polymer components will occur).

The present invention therefore relates to 2 different types of pharmaceutical compositions preferably in the form of injectable solutions containing as the active principle (a), (b1) and/or (b2), and a medicament containing said clathrate, optionally containing a further active ingredient.

Preferably this medicament is given by the association of said pharmaceutical compositions, and contains the clathrate which is formed in situ, at the site of action, said medicament optionally containing another active ingredient.

DESCRIPTION OF THE FIGURES

FIG. 3 represents a schematical spatial representation of the clathrate complexes formed by hyaluronic acid derivative with β-cyclodextrin and the hyaluronic acid derivative with adamantine.

DETAILED DESCRIPTION OF THE INVENTION

Preferred clathrates according to the present invention are those selected from the group consisting of:
clathrate (A), wherein component (a) is a hyaluronic acid derivative with a cyclodextrin, compound (b1) is a hyaluronic acid with amantadine,
clathrate (B), wherein component (a) is a hyaluronic acid with cyclodextrin and (b2) is a water-soluble natural, semisynthetic and synthetic polimer,
clathrate (C), wherein component (a) is hyaluronic acid with amantadine and component (b2) is a polymerised cyclodextrin.

Natural polymers that can be used as component (b2) in clathrate (B) are, for example, collagen, coprecipitates of collagen and glycosaminoglycans, cellulose, polysaccharides such as chitin, chitosan, pectin or pectic acid, agarose, xanthane, gellan, alginic acid ester and slats thereof, polymannan or polyglycans, starch, natural gums.

The semisynthetic polymers that can be used as component (b2) in clathrate (B) can be chosen, for example, from the group consisting of collagen cross-linked with agents such as aldehydes or precursors of the same, dicarboxylic acids or their halogenides, diamines, derivatives of cellulose, hyaluronic acid, chitin, chitosan, gellan, xanthane, pectin or pectic acid, polyglycans, polymannan, agar, agarose, natural gum, glycosaminoglycans.

Lastly, examples of synthetic polymers that can be used as component (b2) in clathrate (B) are, for example, those selected from the group consisting of poloxamers.

A clathrate is an inclusion complex formed by a molecule, namely the guest included in the cage formed by another molecule, namely the host.

In particular, the theory of "clathrate" formation involves a complexation between host and guest molecules described by the following equation:

HOST+GUEST⇌HOST–GUEST.

If the stoichiometry of the interacting molecules [HOST]:[GUEST] (where ⌷designates molar concentration) is equal 1:1, then, in the case of thermodynamic equilibrium the complexation constant—K—can be defined as follows:

$$K = \frac{[\text{HOST} - \text{GUEST}]}{[\text{HOST}] \times [\text{GUEST}]}$$

This equation implies that in the case of equimolar mixture ([HOST]=[GUEST]=1 mol/l), the (molar) concentration of the created complex [HOST–GUEST] depends solely on the magnitude of parameter K.

Figure 1:
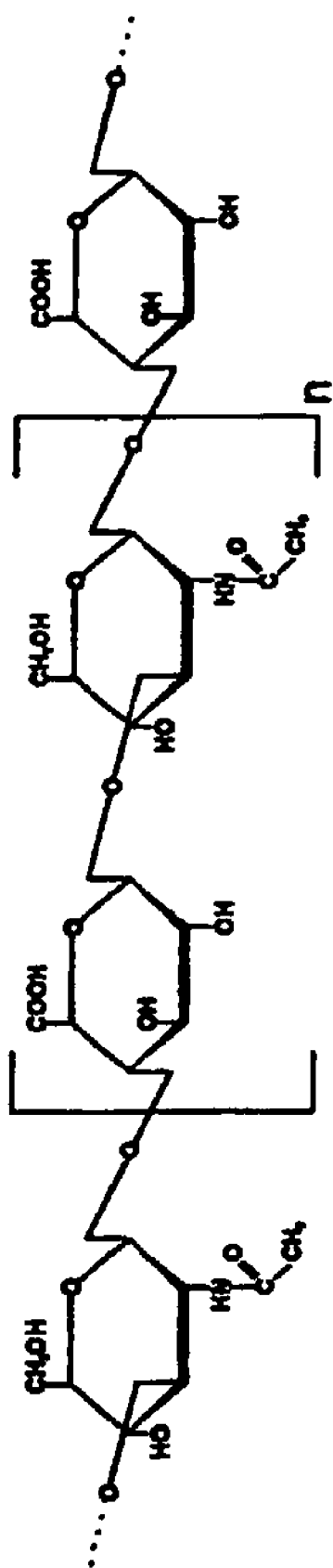
FIG. 1 represents the chemical structure of hyaluronic acid, and β-cyclodextrin.
Figure 2:
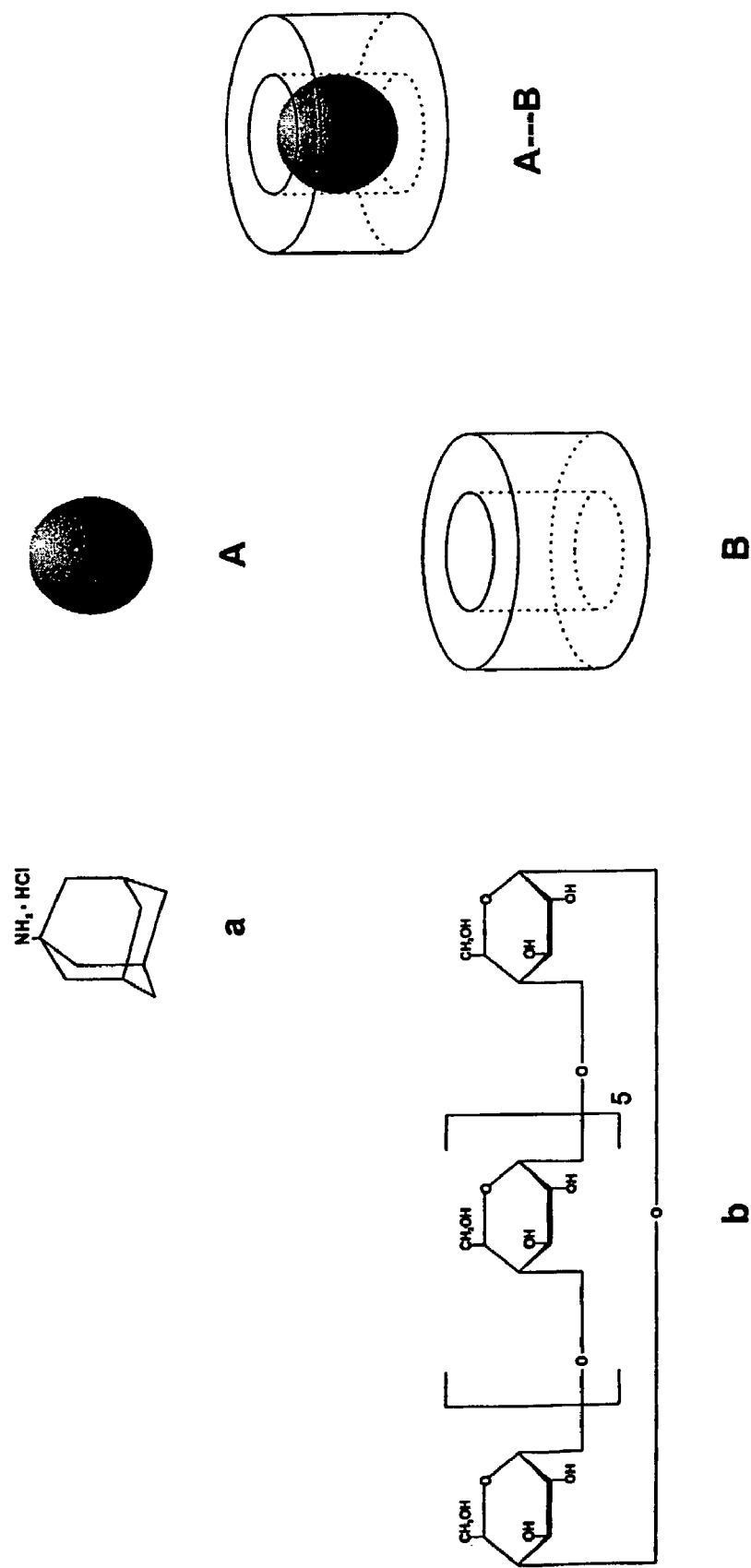
FIG. 2 depicts the chemical structure (a) and schematical spatial representation (A) of amantadine; the chemical structure (b) and the schematical spatial representation (B) of β-cyclodextrin; schematical spatial representation (A-B) of the clathrate complex thereof.

The log K value of complexation of clathrate (A) between β-cyclodextrin (β-CD), where β-CD represents a host, with the guest molecule of amantadine, or in the form of 1-aminoadamantane hydrochloride (AMANT), a drug belonging to the anti-Parkinson disease medications [C. J. Gean and F. H. Meyers, POCKET DRUG GUIDE—Second Ed., Williams & Wilkins, Baltimore, Md., USA, 19 at 25° C., pH 7.2), equals 3.92±0.02 or 5.04 [M. V. Rekharsky and Y. Inoue, Chem. Rev. 98 (1998) 1875]. The complexation process of amantadine molecule with a molecule of β-CD is depicted in FIG. 2.

The adamantyl group (almost spherical in shape) is one of the best guest structures that tightly fits into the host cavity of β-CD molecule [W. C. Cromwell et al, J. Phys. Chem. 89 (1985) 326; C. Amiel and B. Sébille, J. Inclusion Phenom. Mol. Recognit. Chem. 25 (1996) 61]. The value of equilibrium complexation constant K of various adamantane derivatives with non-substituted and substituted β-cyclodextrins lies in the range of $10^4$-$10^5$ mol/l. (One of the highest log K values, 7.8±0.1 (at 25° C.), is obtained with indol complexation with α-CD [M. V. Rekharsky and Y. Inoue, Chem. Rev. 98 (1998) 1875].) FIG. 3 (schematically) depicts the association process of the two derivatives of the high-molecular-weight hyaluronan. Their macromolecular chains bear either substituents of the guest type (AMANT) or of the host type (β-CD), which are able to clinch/pin-up together very tightly (hook and eye-like). In the case of multiple host-quest clinches/pinning-up between the hyaluronan derivatives as it occurs in the case of the clathrate complexes according to the present invention, a stable polymacromolecular associate/aggregate will be formed. In the clathrate according to the present invention the molar ratio of hyaluronic acid derivative with cyclodextrin to hyaluronic acid derivative with amantadine is preferably contained between 10:90 and 90:10, more preferably between 80:20 and 50:50, whereas the molecular weight of this complex is preferably contained for the soft gels between 500 and 25000 kDa, more preferably between 2000 and 20000 kDa. However, for the hard gels, this value exceeds the upper limit and is not determinable.

The molecular weight of the starting hyaluronic acid used for preparing the clathrate according to the present invention is preferably comprised between 100 and 2000 kDa.

The hyaluronic acid derivatives with cyclodextrins are preferably those obtained by direct esterification of the carboxylic group of hyaluronic acid with cyclodextrin, while the substitution occurs on the primary hydroxyl groups (—$CH_2$—OH) of the α-D-glucopyranosyl units of cyclodextrin with a process as described in "Cyclodextrin derivative of hyaluronan" L. Soltes et al (Carbohydrate Polymers 39 (1999) pages 17-24).

According to another preferred embodiment, the hyaluronic acid esters of cyclodextrins are those obtained with cyclodextrins and hyaluronic acids by means of a spacer.

According to a particularly preferred solution the spacer is adipic acid di-hydrazide.

In this case the process for preparing the hyaluronic acid derivatives with cyclodextrin according to the present invention involves:

a) an initial hydrazide group (—CO—NH—NH) formation between adipic acid dihydrazide ($NH_2$—NHCO($CH_2$)$_4$CONH—$NH_2$) and the carboxylic groups of pre-activated hyaluronic acid, and b) the successive reaction between the second hydrazide function ($NH_2$—NHCO—) of the adipic acid dihydrazide derivative of hyaluronic acid with pre-activated primary hydroxyls of cyclodextrin, giving the final product which can be represented as HA—CO—NH—NH—($CH_2$)$_4$—CO—NH—NH—COO—CYCLODEXTRIN.

In this process, step (a) is preferably carried out in the presence of an aqueous buffer solution at pH 5.5 consisting of sodium 2(N-morpholino)-ethanesulfonate and adipic acid di-hydrazide is added to hyaluronic acid activated with 1-ethyl-3(3-dimethyl-aminopropylycarbodiimide. The hyaluronic acid derivative with adipic acid di-hydrazide is preferably recovered from the reaction mixture by dialysis and freeze-drying. Step (b) is preferably carried out by adding adipic acid di-hydrazide derivative of hyaluronic acid to a water solution of cyclodextrin in advance activated with 1-cyano-4-dimethyl-aminopyridinium tetrafluoborate in acetonitrile in the presence of triethylamine, and the reaction is stopped by adding ethanolamine. The product is recovered by dialysis ultrafiltration and by a final freeze-drying. Cyclodextrins for the preparation of the hyaluronic acid derivatives used in clathrate (A) and (B) are preferably selected from the group consisting of: α-cyclodextrin, β-cyclodextrin, γ-cyclodextrin, propyl-β-cyclodextrin, sulfobutyl-β-cyclodextrin, amino or hydrazino-β-cyclodextrin.

These hyaluronic acid derivatives have preferably a degree of substitution of the carboxylic function (namely the percentage of the carboxylic groups of hyaluronic acid reacting with cyclodextrin calculated on the total number of carboxylic acid functions present in said molecule) preferably contained between 0.5 and 50, more preferably between 2 and 20%.

The process for preparing the hyaluronic acid derivatives with amantadine used for preparing the clathrates (A) and (C) according to the present invention comprises in particular the formation of the amidic bond between pre-activated hyaluronic acid and amantadine in an aqueous solution in the presence of a buffer.

According to a preferred embodiment, the amantadine activator is 1-ethyl-3(3-dimethyl-aminopropyl)-carbodiimide and the buffer is sodium 2(N-morpholinoy- ethanesulfonate.

The hyaluronic acid derivatives with amantadine have preferably a degree of substitution (namely the percentage of the carboxylic groups of hyaluronic acid reacting with amantadine calculated on the total number of carboxylic function present in said molecule) comprised between 0.5 and 25, more preferably between 2 and 10%.

The present invention further relates to pharmaceutical compositions containing as the active ingredient a hyaluronic acid derivative with cyclodextrin, or in alternative the hyaluronic acid derivative with amantadine in combination with suitable excipients and/or diluents.

The pharmaceutical compositions according to the present invention may be suitable for oral, parenteral and topical treatment, and may be used in particular in all the fields in which restoration of viscoelasticity is needed, and easiness of injection is also important. They include general surgery (as materials for filling artificial prostheses), maxillofacial surgery (for example as materials for injection to fill wrinkles, in the substitution of soft tissues and for the growth of the tissues), arthroscopic surgery (for example as lubricating materials), or viscosupplementation of the joints even those of smaller size such as phalanges, ankles, temporo-mandibular joints.

Moreover, HA-derivative with cyclodextrin can be used to advantage for the preparation of pharmaceutical forms involving the transport or the controlled release of drugs and/or biologically active substances used in the treatment of disorders in the field of dermatology, ophthalmology, gynaecology, oncology, angiology, neurology, orthopaedics and rheumatology. Such active substances can be anti-infective agents, antimicrobials, anti-inflammatory agents, cytostatic, cytotoxic, antiviral and anaesthetic agents and growth factors. The derivative, in association with radioactive substances and non-radioactive substances, can be used in contrast systems, as label for in vivo diagnostics, to identify and treat tumoral or damaged tissues.

Preparations combining the HA-based biomaterials according to the present invention with drugs and/or biologically active substances are suitable for an innovative therapeutical approach in which the release of the pharmacologically active ingredient is followed by the in situ self-association of the polymer components. The pharmacological activity of the released substance is therefore associated to the lubricating and tissue protecting effect of the in situ cross-linked material. This approach is of advantage in fields such as dermatology, orthopaedics and rheumatology (for example for the therapy of osteoarthritis and rheumatoid arthritis), ophthalmology (for example in the therapy of eye infection and inflammation).

As previously stated, the above mentioned pharmaceutical compositions, for the scope of the present invention are preferably in the form of injectable solutions, and are preferably used in association, thereby giving to the formation of a medicament containing the clathrate according to the present invention, which is formed in situ.

The medicament according to the present invention may contain besides the clathrate also an active ingredient which is preferably selected from the group consisting of nonsteroidal or steroidal anti-inflammatory drugs, antibiotics, antitumorals. These low molecular weight drugs can serve initially as competitors (blockers) of association between the two hyaluronic acid derivatives, and are gradually cleared allowing for clathrate formation.

Particularly preferred is the medicament according to the present invention containing piroxicam.

The medicament according to the present invention may contain in addition or alternative to the aforementioned active ingredients a biologically active substance selected from the group consisting of growth factors, cytokines, and/or cellular material selected from the group consisting of osteocytes, chondrocytes, stem cells and mesenchymal cells.

In the medicament according to the present invention, the active ingredients are preferably coupled with cyclodextrin.

The most promising area of application of the clathrate (HA-based) biomaterials and medicaments is in the patient treatment as well as in improvement of their health management at the diagnoses such as inflammation of joints—arthritis, eye inflammations (conjunctivitis), malignant tumors, skin wounds, etc. The Examples listed below illustrate preparation of the hyaluronic acid derivatives with cyclodextrin and with amantadine, as well as the clathrate formation, but do not limit the scope of the invention.

In the following Examples 1 and 2 the high-molecular-weight hyaluronic acid was used, while in the Examples 3-7 its (sodium) salt.

The molecular parameters of the used HA were as follows: number-average ($M_n$), weight-average ($M_w$), and z-average ($M_z$) molecular weight values: 350.7 (326.5) kDa, 647.1 (659.4; 666.0) kDa, and 1050.4 (1066.1) kDa, respectively. Parameters $<Rg_z^2>^{1/2}$, namely the root-mean-square radius of gyration and $A_2$, namely the second virial coefficient, determined in the aqueous NaCl (0.15 mol/l) were equal 97.4 (97.2)nm and $1.94\times10^{-3}$ mol.ml/$g^2$, respectively.

Example 1

Preparation of HA-β-CD Derivative Using a Spacer

HA (106 mg) is dissolved in aqueous buffer solution of sodium 2-(N-morpholino)-ethanesulfonate (MES; 0,05 mol/l; 57 ml; pH 5.5). A spacer—adipic acid dihydrazide (ADH; 600 mg) and an activator (of the HA carboxylic groups) -1-ethyl-3-(3-dimethyl-aminopropyl) carbodiimide (EDC; 127 mg) were subsequently added to the solution. Upon addition of total EDC, the reaction mixture was dialyzed; and the intermediate HA-ADH was obtained by freeze-drying.

To the-water solution of β-CD (100 mg/30 ml) activator of the hydroxylic groups -1-cyano-4-dimethylaminopyridinium tetrafluoroborate (CDAP; 20 mg) was added in acetonitrile solution (2 ml) with an addition of triethylamine (0.2 mol; pH 7.8). After 2 minutes, aqueous solution of HA-ADH (90 mg/10 ml) was added. Reaction was stopped upon 2 hours with addition of ethanolamine (2 ml). The reaction mixture was dialyzed and the product was subsequently purified by repeated ultrafiltration and finally freeze-dried. (This procedure is suitable for introduction of any homobifunctional spacer that contains (two) terminal amino or hydrazino groups.)

Example 2

The Procedure is identical as in Example 1, however instead of β-cyclodextrin α-CD, γ-CD, or any of the substituted cyclodextrins are used, such as hydroxyethyl-β-CD, hydroxypropyl-β-CD, (partially substituted) sulfobutyl-β-CD, etc.

Example 3

Preparation of HA-β-CD Derivative Using Linkage Through Amino or Hydrazino Group In this application, amino- or hydrazino-derivative of β-CD prepared by the exchange e.g. for the tosyl-group. Reaction of HA with amino- or hydrazino-derivative of β-CD is performed at the conditions identical to those described in Example 1, i.e. using activation of the carboxylic groups of HA with EDC.

Example 4

The procedure is identical as in Example 3, however instead of β-cyclodextrin α-CD or γ-CD is used, etc.

Example 5

Preparation of HA-AMANT Derivative

HA (130 mg) is dissolved in MES buffer (0.05 mol/l; 20 ml; pH 5.5). To the solution at the constant stirring is added amantadine, i.e. 1-amino-adamantane hydrochloride (AMANT; 270 mg), dissolved in 35 ml of the same MES buffer and subsequently EDC, activator of the carboxylic groups of HA, was added (150 mg). Reaction mixture was stirred at the ambient temperature for ca. 20 hours. The pH value was maintained in the range 6.0-6.5 using diluted HCl (0.1 mol/l). Upon termination of the reaction, the solution was filtered (using paper filter "Whatman #3"), the filtrate was further purified using a repeated (5 times) ultrafiltration (using the membrane "Amicon PM-10"). The resulting product (HA-AMANT) was obtained (yield 105 mg) by freeze-drying. The molecular parameters of the prepared HA-AMANT derivative are presented in Table I.

Example 6

Association/host-quest Complexation of the Two (High-molecular-weight) HA Derivatives HA-AMANT (synthesized as described in Example 5) as well as HA-β-CD (synthesized as described in "Cyclodextrin derivative of hyaluronan" L. Soltes et al (Carbohydrate Polymers 39 (1999) pages 17-24)) were dissolved in aqueous NaCl (0.15 mol/l) and mixed in such a way that their molar ratio [HA-AMANT]/[HA-β-CD] was 80:20 or 50:50. The value of the weight-average molecular weight ($M_w$) obtained for the equimolar mixture of the two biopolymers using MALLS was 556.0 kDa, which was significantly higher than the $M_w$ values of the individual components, as well as the simple arithmetic sum of their values (Table I). Similarly, the value $<Rg_z^2>^{1/2}=80.6$ nm determined for the equimolar mixture was substantially higher than those obtained for the separate pure macrobiomolecules, namely 23.8 (25.2) nm for HA-AMANT and 40.2 nm for HA-β-CD.

Example 7

The procedure is identical to that described in Example 6, but in this particular case a solution of the sample prepared as described in Example 6 is mixed with the solution of the sample prepared according to a procedure described in Examples 1-5.

Example 8

Association/host-guest Complexation of HA-alpha-CD Derivative with Polyethylene Glycol Dendrimer HA-alpha-CD (synthesized as described in Example 1) with MW=150 000 Da was dissolved in aqueous NaCl (0.15 mol/l) and mixed with another 0.15 mol/l NaCl solution of polyethylene glycol (PEG) dendrimer (manufactured by Shearwater, USA) of MW=20 000 Da. The weight-average molecular weight of the equimolar mixture of the two biopolymers was 820 000 Da.

Example 9

Association/host/quest Complexation of Polymerized Beta-CD with HA-AMANT

Polymerized beta-CD (manufactured by CYCLOLAB, Hungary) with MW=135000 Da was dissolved in aqueous NaCl (0.15 mol/l) and mixed with another 0.15 mol/l NaCl solution of HA-AMANT (prepared as described in Example 5) of MW=91 200 Da. The weight-average molecular weight of the equimolar mixture of the two biopolymers was 427 000 Da.

TABLE I

Molecular parameters of the synthesized (bio)polymers separately and upon their combination/mixing

| Parameter | HA-β-CD SEC-MALLS | HA-AMANT SEC-MALLS | MALLS | [HA-AMANT]/[HA-β-CD] 80:20 MALLS | [HA-AMANT]/[HA-β-CD] 50:50 MALLS |
|---|---|---|---|---|---|
| $M_z$ (kDa) | 302.9 | 156.1 | | | |
| $M_w$ (kDa) | 185.3 | 86.8 | 91.2 | 293.0 | 556.0 |
| $M_n$ (kDa) | 106.2 | 51.0 | | | |
| $<Rg_z^2>^{1/2}$ (nm) | 40.2 | 23.8 | 25.2 | 69.6 | 80.6 |

From the quantitative aspect, $<Rg_z^2>^{1/2}$ values as well as those of Mw determined for the associates upon the mixing of both biopolymers significantly exceed those found for the separately measured macromolecular components. Since in the case of simple additivity ([1]+[1]) the values obtained for the parameters would be: $<Rg_z^2>^{1/2}$=64.0 (65.4) nm and $M_w$=272.1 (276.5) kDa, the tendency to form larger aggregates upon complexation of both types of macromolecular HA derivatives is significant.

The invention claimed is:

1. A clathrate comprising
   (a) a hyaluronic acid derivatized with at least one host molecule moiety, said host molecule being a cyclodextrin; and
   (b) a hyaluronic acid derivatized with at least one guest molecule moiety, said guest molecule being amantadine.

2. The clathrate according to claim 1, wherein in said (a) hyaluronic acid derivatized with at least one cyclodextrin moiety, the at least one cyclodextrin moiety is bound to hyaluronic acid (HA) through an ester bond between the carboxylic groups of hyaluronic acid and the primary hydroxyl groups (—CH$_2$OH) of the α-D-glucopyranosyl units of cyclodextrin.

3. The clathrate according to claim 1, wherein in said (a) hyaluronic acid derivatized with at least one cyclodextrin moiety, the at least one cyclodextrin moiety is bound to hyaluronic acid (HA) through an adipic acid di-hydrazide moiety.

4. The clathrate according to claim 1, wherein in said (b) hyaluronic acid derivatized with at least one amantadine moiety, the at least one amantadine moiety is bound to hyaluronic acid (HA) through an amide bond between the carboxylic groups of hyaluronic acid and the primary amine groups of amantadine.

5. The clathrate according to claim 1, wherein the cyclodextrin is selected from the group consisting of α-cyclodextrin, β-cyclodextrin, γ-cyclodextrin, propyl-β-cyclodextrin, sulfobutyl-β-cyclodextrin, amino-β-cyclodextrin, and hydrazine-βcyclodextrin.

6. The clathrate according to claim 1, wherein said hyaluronic acid derivatized with at least one cyclodextrin moiety has a degree of substitution between 0.5 and 50%.

7. The clathrate according to claim 6, wherein said degree of substitution is between 2 and 20%.

8. The clathrate according to claim 1, wherein said hyaluronic acid derivative with at least one amantadine moiety has a degree of substitution therefor between 0.5 and 25%.

9. The clathrate according to claim 8, wherein said degree of substitution therefor is between 2 and 10%.

10. The clathrate according to claim 1, wherein the hyaluronic acid prior to being derivatized has a molecular weight between about 100 and about 2000 kDa.

11. The clathrate according to claim 1, having a molecular weight between about 500 and 25000 kDa and the molar ratio of hyaluronic acid with cyclodextrin to hyaluronic acid with amantadine is between 10:90 and 90:10.

12. The clathrate according to claim 11, having a molecular weight between 2000 and 20000 kDa and the molar ratio between 80:20 and 50:50.

13. Hyaluronic acid derivatized with at least one cyclodextrin moiety, said at least one cyclodextrin moiety being bound to hyaluronic acid (HA) through an adipic acid di-hydrazide moiety.

14. Hyaluronic acid derivatized with at least one amantadine moiety, said at least one amantadine moiety being bound to hyaluronic acid (HA) through an amide bond between the carboxylic groups of hyaluronic acid and the primary amine groups of amantadine.

15. A pharmaceutical composition comprising: (1) the hyaluronic acid derivatized with at least one cyclodextrin moiety according to claim 13, as the active ingredient; and (2) pharmaceutically acceptable excipients, diluents, or both.

16. A pharmaceutical composition comprising: (1) the hyaluronic acid derivatized with at least one amantadine moiety according to claim 14, as the active ingredient; and (2) pharmaceutically acceptable excipients, diluents, or both.

17. A medicament comprising (a) a first injectable solution comprising a hyaluronic acid derivatized with at least one cyclodextrin moiety, and (b) a second injectable solution comprising at a hyaloronic acid derivatized with at least one amantadine moiety, wherein the first and second injectable solutions are to be injected to form a clatherate in situ.

18. The medicament according to claim 17, further comprising an active ingredient.

19. The medicament according to claim 18, wherein said active ingredient is selected from the group consisting of nonsteroidal anti-inflammatory drugs, steroidal anti-inflammatory drugs, antibiotics and antitumorals.

20. The medicament according to claim 19, wherein said active ingredient is piroxicam.

21. The medicament according to claim 17, further comprising a biologically active substance selected from the group consisting of growth factors, cytokines, and cellular material.

22. The medicament according to claim 21, wherein the cellular material is selected from the group consisting of osteocytes, chondrocytes, stem cells, and mesenchymal cells.

* * * * *

UNITED STATES PATENT AND TRADEMARK OFFICE
CERTIFICATE OF CORRECTION

PATENT NO.         : 7,563,824 B2
APPLICATION NO.    : 10/220934
DATED              : July 21, 2009
INVENTOR(S)        : Soltes et al.

It is certified that error appears in the above-identified patent and that said Letters Patent is hereby corrected as shown below:

Title page, item (73) Assignee should read as follows:

Assignee: Fidia Farmaceutici S.P.A.
          Abano Terme (Province of Padova) (IT)
          Slovak Academy of Sciences
          84238 Bratislava (SK)

Signed and Sealed this
Twenty-ninth Day of May, 2012

David J. Kappos
*Director of the United States Patent and Trademark Office*